(12) United States Patent
Kantam et al.

(10) Patent No.: US 6,495,726 B1
(45) Date of Patent: Dec. 17, 2002

(54) PROCESS FOR THE PRODUCTION OF BENZALDEHYDE BY THE CATALYTIC LIQUID PHASE AIR OXIDATION OF TOLUENE

(75) Inventors: Mannepalli Lakshmi Kantam; Boyapati Manoranjan Choudary; Pentlavally Sreekanth; Kottapalli Koteswara Rao; Kantarao Naik; Thella Prathap Kumar; Asad Ali Khan, all of Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/414,473

(22) Filed: Oct. 7, 1999

(30) Foreign Application Priority Data

Sep. 16, 1999 (IN) ........................................ 1242/DEL/99

(51) Int. Cl.[7] .............................................. C07C 47/54
(52) U.S. Cl. ........................ 568/431; 568/426; 568/432
(58) Field of Search ................................ 568/426, 431, 568/432

(56) References Cited

FOREIGN PATENT DOCUMENTS

| | | |
|---|---|---|
| CH | 645335 | 9/1984 |

OTHER PUBLICATIONS

Derwent English Abstract of JP 53 005132 Dated Jan. 18, 1978 (XP002134845).

Borgaonkar, H.V. et al. "Liquid Phase Oxidation of Toluene To Benzaldehyde By Air." Ind. Eng. Chem. Prod. Res. Dev., vol. 23, No. 3, (1984) pp. 455–458.

Okada, T. et al. "The Liquid–phase Oxidation of Methylbenzenes By The Cobalt . . . " Bull. Chem. Soc. Jpn., vol. 54, No. 9 (1981) pp 2724–2727.

Gerber, T.I.A. et al. "The Partial Air Oxidation Of Alkyl Aromatic Compounds Catalysed By Cobalt/Bromide . . . " S. AFR. J. Chem., vol. 51, No. 4 (1998) pp. 178–185.

*Primary Examiner*—Sreeni Padmanabhan
(74) *Attorney, Agent, or Firm*—Ladas & Parry

(57) ABSTRACT

The present invention relates to an improved process for the production of benzaldehyde with 40–50% selectivity comprising by catalytic liquid phase air oxidation of toluene. The process involves providing a continuous flow of air in the presence of a catalyst such as salts of Fe, Co, Mo and Ni, and preferably a co-catalyst such as salts of manganese or copper, a promoter which may also be a bromine source, and a carboxylic acid solvent selected from the group consisting of acetic, propionic, benzoic acids ranging between 0.05 to 0.3 wt. times with respect to toluene, at a temperature ranging between 60–130° C. and pressures in the range of 1–10 bars for a period of 0.5–1.5 hours to obtain benzaldehyde (40–50%) along with other by-products.

17 Claims, No Drawings

PROCESS FOR THE PRODUCTION OF BENZALDEHYDE BY THE CATALYTIC LIQUID PHASE AIR OXIDATION OF TOLUENE

FIELD OF THE INVENTION

The present invention relates to a process for the production of benzaldehyde by catalytic liquid phase air oxidation of toluene, preferably with 40–50% selectivity.

The N.F./F.C.C. grade of benzaldehyde is widely used in flavors such as almond and cherry and in various fragrances for soap and toiletries. Benzaldehyde is a F.D.A. sanctioned synthetic flavoring substance generally recognized as safe for food. The technical grade is a versatile chemical intermediate in the manufacture of pharmaceuticals, dyes, perfume and flavoring chemicals. The technical grade of benzoic acid is used as an intermediate in the manufacture of chemicals, alkyd resins, polyesters, plasticizers, dyestuffs, preservatives, rubber activators and retardants. Benzoic acid, industrial grade, is used as a chemical intermediate and as a diverting agent in crude oil recovery applications.

BACKGROUND OF THE INVENTION

Benzaldehyde is currently produced by the hydrolysis of the corresponding side chain halogenated toluene compound. U.S. Pat. No. 4,229,379, Oct. 21, 1980 describes the preparation of benzaldehyde by hydrolysis of benzyl chloride at 100–200° C. at normal or under increased pressures in the presence of an excessive aqueous hydrochloric acid. U.S. Pat. 4,450,298, May 22, 1994, discloses vapour phase catalytic hydrolysis of benzyl chloride to form benzaldehyde by using activated carbon treated with $H_2SO_4$ or impregnated with a metal chloride such as $FeCl_3$ or a metal sulphate such as cupric sulphate. The drawbacks in the above processes are generation of large excess of effluents and the benzaldehyde produced does not meet food grade specifications.

Air oxidation of toluene and its derivatives offers green technology path, provided the desired selectivities are realised for market driven products and minimisation of halogenated and unwanted by-products causing effluents is achieved. Several patents and or applications describe innovation in air oxidation of toluene and its derivatives both in liquid and vapour phase.

One of the prevalent industrial practices for the vapour phase oxidation of toluene to benzaldehyde involves a uranium oxide/molybdenum oxide catalyst at 500–600° C. (W. L. Faith, D. B. Keyes and R. L. Clark, Industrial Chemicals, $3^{rd}$ Ed., John Wiley & Sons, Inc., New York, 1965); (U.S. Pat. No. 3,579,589). U.S. Pat. 3,946,067 discloses a process for the preparation of aromatic aldehydes such as benzaldehyde or substituted benzaldehydes by the vapour-phase oxidation of aralkyl compounds, such as toluene or substituted toluenes, respectively, at temperatures of less than ~250° C. in the presence of a catalyst composition containing phosphoric acid and a catalytically effective amount of palladium metal. The aromatic aldehydes are produced in a single reaction step. The drawbacks in this process are that the conversion of toluene has to be kept very low <4% to attain high selectivity (>70%) of benzaldehyde and significant amount of carbon dioxide is also formed in this process.

U.S. Pat. No. 3,989,674, Nov. 2, 1976 describes a process wherein a mixture of toluene, oxygen and a helium diluent in molar ratio 1:2:8 is passed over the Cu—Au-silica catalyst at atmospheric pressure and temperatures in the range of 450–600° F. with 200–1000 volumes of gas/h/volume of catalyst. The selectivity of benzaldehyde is 75–80% at conversion levels 15–30%. U.S. Pat. No. 4,137,259, Jan. 30, 1979, describes a process for the vapour phase catalytic oxidation of toluene to benzaldehyde and benzoic acid at a temperature ranging from 300–500° C. in the presence of a silver-iron vanadate on silica with conversion 21%. A selectivity to aldehyde of 33% is described. U.S. Pat. No. 4,390,728, Jun. 28, 1983, describes a process wherein benzaldehyde is formed by the oxidation of toluene in the presence of a catalyst composed of the oxides of Cu, Fe, Pb, U, Mo, and P, and optionally including some other promoter elements. The reaction conditions are 475–550° C., 0–10 atm. pressure, per pass conversion is 35–50%, and selectivity to benzaldehyde 40–70%. Ray et al, Ind. J. Technol., 21(4), 137, 1983, reported a process for the oxidation of toluene to benzaldehyde. But, the conversion per pass is restricted to ~15% and the yield of benzaldehyde is generally not more than 70%, with $CO_2$ as main product. Further, the low concentration of toluene in the toluene-air feed mixture poses problems of recovery. The drawbacks in the above processes are the use of higher reaction temperatures, generation of carbon dioxide in large amounts contributing to global warming. Therefore, these processes do not appear to be attractive.

U.S. Pat. No. 5,476,827, Dec. 19, 1995, discloses the preparation of aldehydes by the reduction of acids and esters in vapour phase in the presence of a bimetallic catalyst. The drawback is the two-step process of oxidation of toluene, a desired raw material, to benzoic acid and reduction of benzoic acid to benzaldehyde with hydrogen. Eventually, this process becomes uneconomical, when compared to a process of selective oxidation of toluene to benzaldehyde conceived.

Morimoto et al (J. Chem. Soc. Sect. B, 62, 1967), Fields et al (Adv. Chem. Ser., No. 76 (2), 395) and Kamiya (Adv. Chem. Ser., No. 76 (2), 193, 1968) have reported that liquid phase air oxidation provides high yield of benzaldehyde when oxidation is carried out in acetic acid medium with cobalt acetate as catalyst and sodium bromide as promoter. The drawbacks are that this process suffers from the disadvantages of relatively low yield. U.S. Pat. No. 2,959,613, describes a process wherein the liquid phase oxidation of toluene or its nucleus substituted materials, such as xylene, is carried out by oxygen under the presence of a catalyser containing a bromine compound and a heavy metallic compound (such as a cobalt compound or manganese compound) along with a zinc compound or an alkaline earth metallic compound or an alkaline metallic compound. The drawbacks in this method are that the main product is the corresponding aromatic carbonic acid and either there is absolutely no production of the corresponding aromatic aldehyde or it is produced in a very small quantity as a by-product.

Japanese Patent No. SHO-53-5132 discloses a process wherein in order to increase the selectivity of benzaldehyde or its nucleus substituted material, a large quantity of catalyser containing a cobalt compound and bromine compound is used. Japanese Patent No. SHO-56-108728, Aug. 28, 1981, describes a process wherein the liquid phase air oxidation of toluene is carried out by a catalyst comprising a heavy metallic compound, zinc and bromine compound at 30–180° C. and a small pressure. The transformation percentage of toluene is maintained within a specific range with the advantage of the execution of the reaction employing carboxylic acid as solvent in the range 0.5–2.0 times with respect to toluene or its substituted material. By this method, the selectivity of benzaldehyde is increased while formation of benzyl bromide is reduced to 2 mol %. However, the turnover number is 3–50 in these air oxidation reactions. The drawback in the above processes are that low turnover numbers render the process uneconomical; the use of higher catalyst concentration hasten corrosion of reactors and excessive production of benzyl bromide is detrimental to achieve the desired quality of the product. U.S. Pat. No. 3,969,405 wherein the oxidation of toluene in the presence of cobalt acetate, acid activator and molecular oxygen oxidant giving high yield of benzoic acid with selectivity to benzaldehyde 35% is disclosed. U.S. Pat. No. 5,473,101 describes a process wherein the oxidation of toluene is carried out in the presence of cobalt acetate, sodium bromide and hydrogen peroxide disclosing conversion of 90.6%, benzaldehyde yield of 29.0%, benzoic acid yield of 55.6%. There are drawbacks in the above processes due to excessive production of benzyl bromide or its nucleus substituted material. Therefore, such a method cannot be said to be a satisfactory one from the point of view of industrial production.

Obviously different approaches have been employed both at laboratory and commercial scale to prepare benzaldehyde. Traditional process has the disadvantage of forming unwanted and corrosive halogenated by-products.

OBJECT OF THE INVENTION

The main object of the present invention is to provide an improved process for the production of benzaldehyde with 40–50% selectivity by the catalytic liquid phase air oxidation of toluene.

Another object of the present invention is maintaining transformation percentage <25% in the catalytic liquid phase air oxidation of toluene.

Yet another object of the present invention is the production of benzaldehyde (40–50%) in very low concentration of catalyst thereby rendering the process economical.

Yet another object of the present invention is the production of benzyl alcohol (5–10%) another value added product of toluene in very low concentration of catalyst rendering the process economical.

Yet another object of the invention is to restrict the conversion to obtain high selectivity of benzaldehyde by the termination of the reaction after 1–1.5 hrs.

Yet another object of the present invention is to achieve production of benzaldehyde with a low concentration of catalyst, co-catalyst and promoter thus slowing down corrosion of the reactor which is a very important factor affecting economics of the project.

Yet another object of the present invention is to obtain near identical conversions and selectivities without the addition of promoter or bromide in recycle reactions conducted with the recovered composite mixture of catalyst, co-catalyst and promoter.

Yet another object of the present invention is to minimise the consumption of bromide promoter in recycle reactions.

Yet another object of the invention is to eliminate the formation of benzyl bromide which is detrimental to the quality of benzaldehyde.

Yet another object of the present invention is to provide a process where the turnover number is in the range of 350–700.

Yet another object of the present invention the benzaldehyde produced is chlorine free and can be used for a wide range of applications.

Another object of the present invention is to provide an environmentally safe process by elimination of the effluent disposal problem.

Yet another object of the present invention the benzaldehyde produced is chlorine free and can be used for a wide range of applications.

Another object of the present invention is to provide an environmentally safe process by elimination of the effluent disposal problem.

SUMMARY OF THE INVENTION

Accordingly the present invention provides an improved process for the production of benzaldehyde with 40–50% selectivity comprising carrying out catalytic liquid phase air oxidation of toluene by providing a continuous flow of air in the presence of a catalyst selected from the group consisting of Fe, Co, Mo and Ni, and preferably a co-catalyst selected from manganese and copper salts, a promoter and a bromine source selected from cobalt bromide, sodium bromide and zinc bromide, and a carboxylic acid solvent selected from the group consisting of acetic, propionic, benzoic acids ranging between 0.05 to 0.3 wt. times with respect to toluene, at a temperature ranging between 60–130° C. and pressures in the range of 1–10 bars for a period of 0.5–1.5 hours to obtain benzaldehyde (40–50%) along with other by-products.

The invention also relates a process for the production of benzaldehyde with 40–50% selectivity by catalytic liquid phase air oxidation of toluene which comprises the production of value added products benzaldehyde (40–50%), benzyl alcohol (5–10%) and benzoic acid in large proportions without any trace amounts of benzyl bromide while maintaining transformation percentage <25% in the catalytic liquid phase air oxidation of toluene with continuous flow of air employing the salts of Fe, Co, Mo, Ni as catalysts, manganese or copper salts as co-catalysts and cobalt bromide, sodium bromide and zinc bromide as promoters as well as bromine source and low content of carboxylic acid as solvent such as acetic, propionic, benzoic acids 0.05 to 0.3 wt. times with respect to toluene, in the temperatures 60–130° C. and pressures in the range of 1–10 bars for a period of 0.5–1.5 hrs.

In an embodiment of the present invention the conversion is restricted to 15–25%.

In another embodiment of the present invention the process is a catalytic liquid phase reaction.

In still another embodiment of the present invention the selectivity to benzyl alcohol is 5–10%.

In still another embodiment of the present invention air is used as the oxidant.

In still another embodiment of the present invention the co-catalyst contains a heavy metallic compound such as manganese or copper and concentration with respect to toluene is very low in the range of 0.004–0.017 mol %.

In still another embodiment of the present invention the catalyst and co-catalyst are organic acid salts selected from the group consisting of formic acid salts, acetic acid salts, propionic acid salts, etc. of the heavy metallic compound.

In still another embodiment of the present invention the promoter is a bromine compound such as cobalt, sodium or zinc bromide. The concentration of the promoters in the reaction system with respect to the toluene is very low in the range of 0.14–1.14 mol %.

In yet another embodiment, the promoter used is also a bromine source.

In still another embodiment of the present invention the atomic ratio of zinc atoms with respect to heavy metallic atoms is in the range of 0.05–8.

In still another embodiment of the present invention in recycle reactions conducted with the recovered catalyst, near identical conversions and selectivities were obtained without any addition of promoter or bromide on each recycle.

In still another embodiment of the present invention in recycle reactions conducted, the consumption of promoter is minimised.

In still another embodiment of the present invention the process is conducted with low concentration of catalyst, co-catalyst and promoter in order to slow down corrosion of the reactor.

In still another embodiment of the present invention the turnover number is in the range of 350–700.

In still another embodiment of the present invention the process totally eliminates the formation of benzyl bromide as a by-product.

In still another embodiment of the present invention the benzaldehyde produced is chlorine free and can be used for a wide range of applications.

The process also results in the production of value added byproducts benzyl alcohol (5–10%) and benzoic acid in large proportions without any trace amounts of benzyl bromide while maintaining transformation percentage <25%.

It has now been discovered that there is a high selectivity of benzaldehyde and benzyl alcohols in the air oxidation of toluene, with turnover number 350–700. The low concentration of solvent, carboxylic acid in the reaction minimise the release of HBr, which in turn generates free radical Br on interaction with $Co^{3+}$ sufficient to the initiation of the reaction. In a recycle reaction conducted with the recovered catalyst, near identical conversions and selectivities were obtained without any addition of promoter or bromide. This result clearly establishes that bromine consumption in the system is minimised. An analysis of the results of experiments provides confirmation of the reduced consumption of bromine in the system. Therefore, formation of the by-product, benzyl bromide which requires higher content of HBr is eliminated, thus, resulting in production of benzaldehyde which meets specification of the food grade. This also helps to achieve higher turnover number by allowing optimum use of catalyst and co-catalyst. Apart from this, low concentration of catalyst, co-catalyst and promoter further slows down corrosion on the reactor, a very important factor affecting the economics of process. The process is environmentally safe since there is no effluent disposal problem.

The following examples are given by way of illustration of the present invention and therefore should not be construed to limit the scope of the present invention.

EXAMPLE 1

Buchi glass autoclave of 500 ml capacity equipped with a gas connecting tube, stirrer and pressure gauge was deployed. The following materials were taken in the reaction vessel—99.6 ml of toluene, 200.4 ml of acetic acid, 0.75 g of cobalt acetate.4 water salt, 2.5 g of sodium bromide. After flushing thrice with air, the solution was heated slowly up to 110° C. while stirring the reaction mixture. After system attained a constant temperature of 110° C., it was pressurised with air to 9 $Kg/cm^2$ with 2 Lt/min out flow. After 2 hrs, the reaction mixture was taken out. Gas chromatographic and titrimetric analysis on the product indicates conversion of 20.43% with selectivity towards benzaldehyde 40.98%, benzyl alcohol 0.79%, benzoic acid 58.24%.

EXAMPLE 2

Buchi glass autoclave of 500 ml capacity equipped with a gas connecting tube, stirrer and pressure gauge was deployed. The following materials were taken in the reaction vessel; 107 ml of toluene, 193 ml of acetic acid, 5 g of cobalt acetate.4 water salt, 0.3 g of manganese acetate.4 water salt, 9 g of zinc bromide. After flushing thrice with air, the solution was heated slowly up to 80° C. while stirring the reaction mixture. After system attained a constant temperature of 80° C., it was pressurised with air to 9 $Kg/cm^2$ with 2 Lt/min out flow. After 1.15 hrs, the reaction mixture was taken out. Gas chromatographic and titrimetric analysis on the product indicates conversion of 13.2% with selectivity towards benzaldehyde 62.77%, benzyl alcohol 2.75% and benzoic acid 34.46%.

EXAMPLE 3

Buchi glass autoclave of 500 ml capacity equipped with a gas connecting tube, stirrer and pressure gauge was deployed. The following materials were taken in the reaction vessel—150 ml of toluene, 150 ml of acetic acid, 1.5 g of cobalt acetate.4 water salt, 5 g of sodium bromide. After flushing thrice with air, the solution was heated slowly up to 110° C. while stirring the reaction mixture. After system attained a constant temperature of 110° C., it was pressurised with air to 9 $Kg/cm^2$ with 2 Lt/min out flow. After 2.15 hrs, the reaction mixture was taken out. Gas chromatographic and titrimetric analysis on the product indicates conversion of 15.17% with selectivity towards benzaldehyde 49.95%, benzyl alcohol 3.25% and benzoic acid 46.8%.

EXAMPLE 4

Buchi glass autoclave of 500 ml capacity equipped with a gas connecting tube, stirrer and pressure gauge was deployed. The following materials were taken in the reaction vessel—280 ml of toluene, 20 ml of acetic acid, 1.5 g of cobalt acetate.4 water salt, 5 g of sodium bromide. After flushing thrice with air, the solution was heated slowly up to 110° C. while stirring the reaction mixture. After system attained a constant temperature of 110° C., it was pressurised with air to 9 $Kg/cm^2$ with 2 Lt/min out flow. After 2.15 hrs, the reaction mixture was taken out. Gas chromatographic and titrimetric analysis on the product indicates conversion of 9.22% with selectivity towards benzaldehyde 46.23%, benzyl alcohol 10.25%, benzoic acid 43.51%.

EXAMPLE 5

Buchi glass autoclave of 500 ml capacity equipped with a gas connecting tube, stirrer and pressure gauge was deployed. The following materials were taken in the reaction vessel—224.3 ml of toluene, 75.7 ml of acetic acid, 1.5 g of cobalt acetate.4 water salt 5 g of sodium bromide. After flushing thrice with air, the solution was heated slowly up to 110° C. while stirring the reaction mixture. After system attained a constant temperature of 110° C., it was pressurised with air to 9 $Kg/cm^2$ with 2 Lt/min out flow. After 2.15 hrs, the reaction mixture was taken out. Gas chromatographic and titrimetric analysis on the product indicates conversion of 17.4% with selectivity towards benzaldehyde 43.48%, benzyl alcohol 4.37% and benzoic acid 52.15%.

EXAMPLE 6

Buchi glass autoclave of 500 ml capacity equipped with a gas connecting tube, stirrer and pressure gauge was deployed. The following materials were. taken in the reaction vessel, 224.3 ml of toluene, 75.7 ml of acetic acid, 1.5 g of cobalt acetate.4 water salt, 0.09 g of manganese acetate.4 water salt, 5.4 g of zinc bromide. After flushing thrice with air, the solution was heated slowly up to 80° C. while stirring the reaction mixture. After system attained a constant temperature of 80° C., it was pressurised with air to 9 Kg/cm$^2$ with 2 Lt/min out flow. After 2 hrs, the reaction mixture was taken out. Gas chromatographic and titrimetric analysis on the product indicates conversion of 10.32% with selectivity towards benzaldehyde 59.47%, benzyl alcohol 6.23% and benzoic acid 34.29%.

EXAMPLE 7

Buchi glass autoclave of 500 ml capacity equipped with a gas connecting tube, stirrer and pressure gauge was deployed. The following materials were taken in the reaction vessel; 225.3 ml of toluene, 75.7 ml of acetic acid, 1.5 g of cobalt acetate.4 water salt, 0.09 g of manganese acetate.4 water salt, 2.7 g of zinc bromide. After flushing thrice with air, the solution was heated slowly up to 110° C. while stirring the reaction mixture. After system attained a constant temperature of 110° C., it was pressurised with air to 9 Kg/cm$^2$ with 2 Lt/min out flow. After 1.45 hrs, the reaction mixture was taken out. Gas chromatographic and titrimetric analysis on the product indicates conversion of 16.36% with selectivity towards benzaldehyde 39.6%, benzyl alcohol 5.53%, and benzoic acid 54.8%.

EXAMPLE 8

Buchi glass autoclave of 500 ml capacity equipped with a gas connecting tube, stirrer and pressure gauge. The following materials were taken in the reaction vessel; 224.3 ml of toluene, 75.7 ml of acetic acid, 1.12 g of cobalt acetate.4 water salt, 0.06 g of manganese acetate.4 water salt, 2.02 g of zinc bromide. After flushing thrice with air, the solution was heated slowly up to 110° C. while stirring the reaction mixture. After system attained a constant temperature of 110° C., it was pressurised with air to 9 Kg/cm$^2$ with 2 Lt/min out flow. After 1.15 hrs, the reaction mixture was taken out. Gas chromatographic and titrimetric analysis on the product indicates conversion of 11.06% with selectivity towards benzaldehyde 39.94%, benzyl alcohol 8.9%, benzoic acid 51.14%.

EXAMPLE 9

Buchi glass autoclave of 500 ml capacity equipped with a gas connecting tube, stirrer and pressure gauge was deployed. The following materials were taken in the reaction vessel; 224.3 ml of toluene, 75.7 ml of acetic acid, 1.12 g of cobalt acetate.4 water salt, 0.06 g of manganese acetate.4 water salt, 1.01 g of zinc bromide. After flushing thrice with air, the solution was heated slowly up to 110° C. while stirring the reaction mixture. After system attained a constant temperature of 110° C., it was pressurised with air to 9 Kg/cm$^2$ with 2 Lt/min out flow. After 1.15 hrs, the reaction mixture was taken out. Gas chromatographic and titrimetric analysis on the product indicates conversion of 14.22 % with selectivity towards benzaldehyde 36.40%, benzyl alcohol 8.91% and benzoic acid 54.68%.

EXAMPLE 10

Catalyst Recycle

The reaction mixture of example 9 containing toluene, acetic acid, benzaldehyde, benzoic acid, benzyl alcohol and catalyst mixture was taken for recycle study. Water was then added to the reaction mixture while it is hot after recovering toluene and acetic acid by distillation and then cooled to room temperature. Benzoic acid formed was removed by filtration and the remaining organic and aqueous layers were separated. Organic layer was subjected to distillation to get benzaldehyde and benzyl alcohol and the aqueous layer is concentrated to get the catalyst composite mixture cake.

Buchi glass autoclave of 500 ml capacity equipped with a gas connecting tube, stirrer and pressure gauge was deployed. The following materials were taken in the reaction vessel; 224.3 ml of toluene, 75.7 ml of acetic acid, recovered composite mixture cake containing cobalt acetate, manganese acetate and zinc bromide. After flushing thrice with air, the solution was heated slowly up to 110° C. while stirring the reaction mixture. After system attained a constant temperature of 110° C., it was pressurised with air to 9 Kg/cm$^2$ with 2 Lt/min out flow. After 1.15 hrs, the reaction mixture was taken out. Gas chromatographic and titrimetric analysis on the product indicates conversion of 11.42% with selectivity towards benzaldehyde 35.40%, benzyl alcohol 11.39% and benzoic acid 53.18%.

EXAMPLE 11

Buchi glass autoclave of 500 ml capacity equipped with a gas connecting tube, stirrer and pressure gauge was deployed. The following materials were taken in the reaction vessel—224.3 ml of toluene, 75.7 ml acetic acid, 0.75 g of cobalt acetate.4 water salt, 0.04 g of manganese acetate.4 water salt, 1.35 g of zinc bromide. After flushing thrice with air, the solution was heated slowly up to 110° C. while stirring the reaction mixture. After system attained a constant temperature of 110° C,. it was pressurised with air to 9 Kg/cm$^2$ with 2 Lt/min out flow. After 2 hrs, the reaction mixture was taken out. Gas chromatographic and titrimetric analysis on the product indicates conversion of 12.75% with selectivity towards benzaldehyde 44.71%, benzyl alcohol 5.15% and benzoic acid 50.1%.

EXAMPLE 12

Buchi glass autoclave of 500 ml capacity equipped with a gas connecting tube, stirrer and pressure gauge was deployed. The following materials were taken in the reaction vessel; 224.3 ml of toluene, 75.7 ml of acetic acid, 0.375 g of cobalt acetate.4 water salt, 0.0225 g of manganese acetate .4 water salt, 0.675 g of zinc bromide. After flushing thrice with air, the solution was heated slowly up to 130° C. while stirring the reaction mixture. After system attained a constant temperature of 130° C., it was pressurised with air to 9 Kg/cm$^2$ with 2 Lt/min out flow. After 2.30 hrs, the reaction mixture was taken out. Gas chromatographic and titrimetric analysis on the product indicates conversion of 10.60% with selectivity towards benzaldehyde of 40.32%, benzyl alcohol 3.19%, benzoic acid 56.40%.

EXAMPLE 13

Buchi glass autoclave of 500 ml capacity equipped with a gas connecting tube, stirrer and pressure gauge was deployed. The following materials were taken in the reaction vessel; 260 ml of toluene, 46 g of benzoic acid, 1.5 g of cobalt acetate.4 water salt, 0.09 g of manganese acetate.4 water salt, 2.7 g of zinc bromide. After flushing thrice with air, the solution was heated slowly up to 130° C. while stirring the reaction mixture. After system attained a constant temperature of 130° C., it was pressurised with air to 9 Kg/cm$^2$ with 2 Lt/min out flow. After 1 hr, the reaction mixture was taken out. Gas chromatographic and titrimetric analysis on the product indicates conversion of 8.69 % with selectivity towards benzaldehyde of 39.97%, benzyl alcohol 7.99%, benzoic acid 51.84%.

EXAMPLE 14

Buchi glass autoclave of 500 ml capacity equipped with a gas connecting tube, stirrer and pressure gauge was deployed. The following materials were taken in the reaction vessel; 280 ml of toluene, 25.52 g of benzoic acid, 1.5 g of cobalt acetate.4 water salt, 0.09 g of manganese acetate.4 water salt, 2.7 g of zinc bromide. After flushing thrice with air, the solution was heated slowly up to 130° C. while stirring the reaction mixture. After system attained a constant temperature of 130° C., it was pressurised with air to 9 Kg/cm² with 2 Lt/min out flow. After 1.30 hr, the reaction mixture was taken out. Gas chromatographic and titrimetric analysis on the product indicates conversion of 6.38% with selectivity towards benzaldehyde of 39.5%, benzyl alcohol 4.9% and benzoic acid 55.44%.

EXAMPLE 15

Buchi glass autoclave of 500 ml capacity equipped with a gas connecting tube, stirrer and pressure gauge was deployed. The following materials were taken in the reaction vessel; 280 ml of toluene, 12.76 g of benzoic acid, 1.5 g of cobalt acetate.4 water salt, 0.09 g of manganese acetate.4 water salt and 2.7 g of zinc bromide. After flushing thrice with air, the solution was heated slowly up to 130° C. while stirring the reaction mixture. After system attained a constant temperature of 130° C., it was pressurised with air to 9 Kg/cm² with 2 Lt/min out flow. After 1.30 hr, the reaction mixture was taken out. Gas chromatographic and titrimetric analysis on the product indicates conversion of 6.79% with selectivity towards benzaldehyde of 36.2%, benzyl alcohol 8.3%, and benzoic acid 55.4%.

EXAMPLE 16

Buchi glass autoclave of 500 ml capacity equipped with a gas connecting tube, stirrer and pressure gauge was deployed. The following materials were taken in the reaction vessel; 260 ml of toluene, 46 g of benzoic acid, 3 ml of water, 0.75 g of cobalt acetate.4 water salt, 0.04 g of manganese acetate.4 water salt and 1.35 g of zinc bromide. After flushing thrice with air, the solution was heated slowly up to 130° C. while stirring the reaction mixture. After system attained a constant temperature of 130° C., it was pressurised with air to 9 Kg/cm² with 2 Lt/min out flow. After 1.30 hr, the reaction mixture was taken out. Gas chromatographic and titrimetric analysis on the product indicates conversion of 4.7% with selectivity towards benzaldehyde of 36.11%, benzyl alcohol 8.14%, benzoic acid 55.48%.

EXAMPLE 17

Buchi glass autoclave of 500 ml capacity equipped with a gas connecting tube, stirrer and pressure gauge was deployed. The following materials were taken in the reaction vessel; 260 ml of toluene, 46 g of benzoic acid, 3 ml of water, 1.5 g of cobalt acetate.4 water salt, 0.09 g of manganese acetate.4 water salt and 2.7 g of zinc bromide. After flushing thrice with air, the solution was heated slowly up to 130° C. while stirring the reaction mixture. After system attained a constant temperature of 130° C., it was pressurised with air to 9 Kg/cm² with 2 Lt/min out flow. After 1.30 hr, the reaction mixture was taken out. Gas chromatographic and titrimetric analysis on the product indicates conversion of 14.86% with selectivity towards benzaldehyde of 24.28%, benzyl alcohol 2.00%, benzoic acid 73.72%. The results are given in Table 1.

TABLE 1

| Ex. No. | Toluene (ml) (w/v %) | AcOH (ml) | Co. Ac (gms) | Mn. Ac (gms) | NaBr (gms) | ZnBr₂ (Gms) | Time (hrs) | Temp (° C.) | Conv (%) | Ald. (%) | Alc. (%) | Acid (%) |
|---|---|---|---|---|---|---|---|---|---|---|---|---|
| 1 | 99.6 (28.56) | 200.4 | 0.75 | — | 2.5 | — | 2 | 110 | 20.43 | 40.98 | 0.79 | 58.24 |
| 2 | 107 (30.67) | 193 | 5 | 0.3 | — | 9 | 1.15 | 80 | 13.2 | 62.77 | 2.75 | 34.46 |
| 3 | 150 (42.88) | 150 | 1.5 | — | 5 | — | 2.15 | 110 | 15.17 | 49.95 | 3.25 | 46.8 |
| 4 | 280 (80.27) | 20 | 1.5 | — | 5 | — | 2.15 | 110 | 9.22 | 46.23 | 10.28 | 43.51 |
| 5 | 224.3 (64.32) | 75.7 | 1.5 | — | 5 | — | 2.15 | 110 | 17.4 | 43.48 | 4.37 | 52.15 |
| 6 | 224.3 (64.32) | 75.7 | 1.5 | 0.09 | — | 5.4 | 2 | 80 | 10.32 | 59.47 | 6.23 | 34.29 |
| 7 | 224.3 (64.32) | 75.7 | 1.5 | 0.09 | — | 2.7 | 1.45 | 110 | 16.36 | 39.6 | 5.53 | 54.8 |
| 8 | 224.3 (64.32) | 75.7 | 1.12 | 0.06 | — | 2.02 | 1.15 | 110 | 11.06 | 39.94 | 6.62 | 51.14 |
| 9 | 224.3 (64.32) | 75.7 | 1.12 | 0.06 | — | 1.01 | 1.15 | 110 | 14.22 | 36.40 | 8.91 | 54.68 |
| 10 | 224.3 (64.32) | 75.7 | Recovered Catalyst | | | | 1.15 | 110 | 11.42 | 35.40 | 11.39 | 53.18 |
| 11 | 224.3 (64.32) | 75.7 | 0.75 | 0.04 | — | 1.35 | 2 | 110 | 12.75 | 44.71 | 5.15 | 50.1 |
| 12 | 224.3 (64.32) | 75.7 | 0.375 | 0.0225 | — | 0.675 | 2.30 | 130 | 10.60 | 40.32 | 3.19 | 56.40 |
| 13 | 260 | B. Acid 46 | 1.5 | 0.09 | — | 2.7 | 1 | 130 | 8.69 | 39.97 | 7.99 | 51.84 |
| 14 | 280 | 25.52 | 1.5 | 0.09 | — | 2.7 | 1.30 | 130 | 6.38 | 39.5 | 4.9 | 55.44 |
| 15 | 280 | 12.76 | 1.5 | 0.09 | — | 2.7 | 1.30 | 130 | 6.79 | 36.2 | 8.3 | 55.4 |
| 16 | 260 | 46 (3 ml) | 0.75 | 0.04 | — | 1.35 | 1.30 | 130 | 4.7 | 36.11 | 8.14 | 55.48 |

TABLE 1-continued

| Ex. No. | Toluene (ml) (w/v %) | AcOH (ml) | Co. Ac (gms) | Mn. Ac (gms) | NaBr (gms) | ZnBr$_2$ (Gms) | Time (hrs) | Temp (° C.) | Conv (%) | Ald. (%) | Alc. (%) | Acid (%) |
|---|---|---|---|---|---|---|---|---|---|---|---|---|
| 17 | 260 | 46 (3 ml) | 1.5 | 0.09 | — | 2.7 | 1.30 | 130 | 14.86 | 24.28 | 2.00 | 73.72 |

The main advantages of the present invention are:
1. The process is a catalytic liquid phase reaction.
2. The selectivity for benzaldehyde obtained in this process is in the range of 40–50%.
3. The selectivity for benzyl alcohol obtained in this process is in the range of 5–10%.
4. Low concentration of catalyst, co-catalyst and promoter is used.
5. The temperatures and pressures employed in the reaction are moderate.
6. The residence time in the reactor is short.
7. Acetic acid is used as the solvent and the amount used is in the range of 0.05 to 0.3 wt. times with respect to toluene.
8. An eco-friendly process for the production of benzaldehyde without the formation of benzyl bromide was developed.
9. Benzaldehyde produced is free from chlorine and can be used over a wide range of applications.
10. High turnover number 350–700 is realised for the first time.
11. The catalytic system afforded recyclability without any addition of promoter thereby utilisation of the promoter in the process on each recycle is minimised.
12. Employment of the low concentration catalytic system slows down corrosion on the reactor, a very important factor affecting economics of the project.
13. The present process is environmentally safe since there is no effluent disposal problem.
14. The process is economical.

We claim:

1. An improved process for the production of benzaldehyde with 40–50% selectivity comprising carrying out catalytic liquid phase air oxidation of toluene by providing a continuous flow of air in the presence of a catalyst selected from the group consisting of salts of Fe, Co, Mo and Ni and a co-catalyst selected from the group consisting of manganese and copper salts, a promoter and a bromine source selected from cobalt bromide, sodium bromide and zinc bromide, and a carboxylic acid solvent selected from the group consisting of acetic, propionic, benzoic acids ranging between 0.05 to 0.3 wt. times with respect to toluene, at a temperature ranging between 60–130° C. and pressures in the range of 1–10 bars for a period of 0.5–1.5 hours to obtain benzaldehyde (40–50%) along with other by-products.

2. A process as claimed in claim 1 wherein the by-products obtained are benzyl alcohol in an amount of 5–10% and benzoic acid.

3. A process as claimed in claim 1 wherein the promoter is selected from the group consisting of cobalt bromide, sodium bromide and zinc bromide.

4. A process as claimed in claim 1 wherein the promoter used is also a bromine source.

5. A process as claimed in claim 1 wherein the turnover number is 350–700.

6. A process as claimed in claim 1 wherein the recovered catalyst is recycled in to the reaction system without any addition of promoter or bromide.

7. A process as claimed in claim 1 wherein the catalyst contains a heavy metallic compound such as cobalt, molybdenum or iron.

8. A process as claimed in claim 1 wherein the concentration of the catalyst with respect to toluene in the reaction system is in the range of 0.07–0.28 mol %.

9. A process as claimed in claim 1 wherein the co-catalyst contains a heavy metallic compound such as manganese or copper and concentration of said co-catalyst with respect to toluene is in the range of 0.004–0.017 mol %.

10. A process as claimed in claim 1 wherein the catalyst and co-catalyst are selected from the group consisting of organic acid salts such as formic acid salts, acetic acid salts, propionic acid salts of said heavy metallic compound.

11. A process as claimed in claim 1 wherein the formation of benzyl bromide as a byproduct is totally eliminated.

12. A process as claimed in claim 1 wherein the concentration of the promoters in the reaction system with respect to the toluene is in the range of 0.14–1.14 mol % and wherein the atomic ratio of zinc atoms with respect to heavy metallic atoms is in the range of 0.05–8.

13. An improved process for the production of benzaldehyde with benzyl alcohol (5 to 10%) and benzoic acid as by-products with 40 to 50% selectivity which comprises subjecting toluene to catalytic liquid phase air oxidation by providing a continuous flow of air in the presence of a catalyst selected from salts of Fe, Co, Mn, Mo, Ni, a co-catalyst selected from manganese or copper salts, a promoter and a bromine source selected from cobalt bromide, sodium bromide and zinc bromide, and a carboxylic acid solvent selected from acetic, propionic and benzoic acids ranging between 0.05 to 0.3 wt. times with respect to toluene, at a temperature ranging between 60 to 130° C. and pressure in the range of 1 to 10 bars for a period of 0.5 to 1.5 hrs.

14. A process as claimed in claim 13 wherein catalyst and co-catalyst are organic acid salts selected from the group consisting of formic acid salts, acetic acid salts, propionic acid salts.

15. A process as claimed in claim 13 wherein the concentration of manganese or copper in the co-catalyst is in a concentration with respect to toluene in the range of 0.004 to 0.017 mol %.

16. A process as claimed in claim 13 wherein the concentration of the catalyst with respect to toluene in the reaction system is in the range of 0.07 to 0.28 mol %.

17. A process as claimed in claim 13 wherein the concentration of the promoters in the reaction system with respect to the toluene is in the range of 0.14 to 1.14 mol % and wherein the atomic ratio of zinc atoms with respect to heavy metallic atoms is in the range of 0.05 to 8.

* * * * *